(12) United States Patent
Fabries

(10) Patent No.: US 9,333,186 B2
(45) Date of Patent: May 10, 2016

(54) DERMO-COSMETIC COMPOSITION FOR PETS

(75) Inventor: Lionel Fabries, Castres (FR)

(73) Assignee: LABORATOIRE DE DERMO-COSMETIQUE ANIMALE (L.D.C.A) SAS, Castres (FR)

( * ) Notice: Subject to any disclaimer, the term of this patent is extended or adjusted under 35 U.S.C. 154(b) by 491 days.

(21) Appl. No.: 13/025,656

(22) Filed: Feb. 11, 2011

(65) Prior Publication Data

US 2011/0195137 A1   Aug. 11, 2011

Related U.S. Application Data

(63) Continuation-in-part of application No. 10/574,760, filed as application No. PCT/FR2004/002518 on Oct. 6, 2004, now abandoned.

(30) Foreign Application Priority Data

Oct. 6, 2003   (FR) ..................................... 03 11687

(51) Int. Cl.

| A61K 36/00 | (2006.01) |
|---|---|
| A61K 31/202 | (2006.01) |
| A61K 8/92 | (2006.01) |
| A61K 9/00 | (2006.01) |
| A61K 31/335 | (2006.01) |
| A61K 31/352 | (2006.01) |
| A61K 31/4166 | (2006.01) |
| A61K 45/06 | (2006.01) |
| A61Q 19/00 | (2006.01) |

(52) U.S. Cl.
CPC ............... *A61K 31/202* (2013.01); *A61K 8/922* (2013.01); *A61K 8/925* (2013.01); *A61K 9/0017* (2013.01); *A61K 31/335* (2013.01); *A61K 31/352* (2013.01); *A61K 31/4166* (2013.01); *A61K 36/00* (2013.01); *A61K 45/06* (2013.01); *A61Q 19/00* (2013.01)

(58) Field of Classification Search
None
See application file for complete search history.

(56) References Cited

U.S. PATENT DOCUMENTS

| 4,018,932 A | * | 4/1977 | Spicer et al. ................... 514/368 |
| 6,149,932 A | * | 11/2000 | Allen ............................. 424/439 |
| 2003/0083309 A1 | * | 5/2003 | Adeyeye et al. ................. 514/54 |

FOREIGN PATENT DOCUMENTS

| EP | 856304 A2 | * | 8/1998 |
| FR | 2371201 A | * | 7/1978 |
| JP | 2002047182 A | * | 2/2002 |

* cited by examiner

*Primary Examiner* — Qiuwen Mi
(74) *Attorney, Agent, or Firm* — Egbert Law Offices, PLLC

(57) ABSTRACT

The invention relates to a method of treating the coat of an animal. The method includes the steps of applying a composition to the coat of the animal, diffusing the composition by action of a carrier, storing the active ingredients of the composition by the sebaceous glands of the animal, and gradually releasing the active ingredients from the sebaceous glands. The dermo-cosmetic composition includes a diffusion solvent vehicle that enables, by a simple application to one or more points of the cutaneous surface, a diffusion over the entirety thereof and at the level of the sebaceous glands. The active ingredients, primarily including a complex of essential oils and of polyunsaturated fatty acids, stored in these sebaceous glands can be salted out progressively with the sebum product to the surface of the skin.

13 Claims, No Drawings

DERMO-COSMETIC COMPOSITION FOR PETS

RELATED U.S. APPLICATIONS

The present application is a Continuation-In-Part of U.S. application Ser. No. 10/574,760, filed on Mar. 28, 2008, presently pending.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

This invention concerns a method of treating the coat of an animal. More particularly, the invention concerns a method of applying a dermo-cosmetic composition for pets (including new "NAC" pets.)

BACKGROUND OF THE INVENTION

Veterinary dermatology products for animal preventive or maintenance usage are generally designed in the form of creams, lotions or shampoos. Their application to animals is always delicate and sometimes unpleasant for them. The user's normal trend is often to overdose the quantity of product applied as it is frequently the case for lotions and powders, which causes some disturbance in the animal.

Powders, shampoos or lotions often have a localized effect, which does not make it possible to cover in one single application all needs for a dermo-cosmetic treatment, which include: skin care and hydration; soothing effects; deodorant effects; sanitizing and purifying effects; antioxidant and anti-radical effects; and insect repellent effect.

The purpose of this invention is to eliminate these disadvantages by achieving a method and composition which is easier to apply and that in its most elaborate formulation can meet many basic needs of an animal dermo-cosmetic treatment.

The method under the invention makes it possible after a localized application to diffuse the active ingredients over the whole surface through the diffusion carrier solvent. Then the invention uses the capacity of the sebaceous glands to store in certain conditions the treatment active ingredients and to gradually release them through the natural production of sebum.

To that effect, the dermo-cosmetic composition of the method of the present invention, using the capacity of the sebaceous glands to store the active ingredient(s) and to diffuse them through the sebum, is characterized mainly in that it comprises at least: a carrier that is a solvent, and a complex of essential oils is selected by themselves or in combination based on the effects to be achieved.

This combination makes it possible to propose a composition ready for use made mainly of a carrier that is a solvent and of essential oils that, once applied in one or more locations of the animal coat, achieves treatment over the whole skin surface of the animal for several days. Tests performed showed that a result was achieved within 7 days minimum.

According to another characteristic of the invention, the solvent making up the carrier is an ethoxydiglycol.

According to another characteristic, the composition comprises: a carrier consisting of an organic solvent, a complex of essential oils, and polyunsaturated fatty acids used locally in animals.

According to a further characteristic of the invention, the above-described composition can contain a soothing agent and/or an anti-inflammatory and/or anti-pruriginous agent.

Other advantages and characteristics of the invention will become obvious when reading the description below.

The purpose of the composition under the invention is to achieve a treatment of animal skin that has several effects which include: prevention and hydration; soothing effects; deodorant effects; sanitizing and purifying effects; antioxidant and anti-radical effects; and insect-repellent effect.

The advantage of the invention is to be able to combine all or part of the above effects based on the complexity of the composition from an application over a limited area of the animal skin.

These and other objects and advantages of the present invention will become apparent from a reading of the attached specification and appended claims.

BRIEF SUMMARY OF THE INVENTION

The present invention is a method of treating a coat of an animal including the steps of applying a composition to at least one specific location on the coat of the animal, the composition having a carrier being a solvent and at least one complex of essential oils, the composition having active ingredients. The composition is diffused by an action of said carrier. The active ingredients of the composition are stored by sebaceous glands of the animal. Finally, the active ingredients are gradually released from the sebaceous glands.

The solvent may be ethoxydiglycol. The carrier may be an organic solvent selected from the group consisting of acetone, acetonitrile, benzyl alcohol, butyldiglycol, dimethyl acetamide, dimethyl formamide, dipropylene glycol monobutyl ether, ethanol, isopropanol, methanol, ethylene glycol monoethyl ether, monoethyl acetamide, dipropylene glycol monomethyl ether, liquid polyoxyethylene-glycol, propylene glycol, 2-pyrrolidone including N-methylpyrrolidone, diethyelene glycol monoethyl ether, ethylene glycol, diethyl phthalate, and mixtures thereof.

In one embodiment, the composition may be polyunsaturated essential fatty acids. The fatty aids may be hemp oils in a proportion of 1 to 15% by weight of the total composition. These fatty acids may be selected from a group consisting of fish oil, borage oil, coconut oil, kukui oil, sesame oil, reconstituted synthetic polyunsaturated fatty acids, eicosapentaenoic acid, docosahexaenoic acid, shea butter, olive oil, canola oil, walnut oil, soybean oil, and anchusa oil in a proportion of 3 to 50% by weight of the total composition. In one embodiment, the composition may further include a soothing agent, the fatty acids being omega 3 and omega 6. The composition may also include an anti-inflammatory agent, the fatty acids being omega 3 and omega 6. The composition may also include an anti-pruriginous agent, the fatty acids being omega 3 and omega 6.

Where the composition includes an anti-inflammatory agent, it may be selected from a group consisting of bisabolol, azulene, allantoin, glycyrrhetinic 18 beta acid and its salts, aloe extracts, *calendula* extracts, and carrot extracts in a proportion of 0.01 to 10% by weight of the total composition.

In one embodiment, the method further includes a thickening or stabilizing crystallization-inhibiting film-forming agent selected from a group consisting of polyvinyl pyrrolidone, hydroxymethyl cellulose, polyvinyl alcohols, vinyl acetate and vinyl pyrrolidone copolymers, polyethylene glycols, benzyl alcohol, mannitol, glycerol, sorbitol, polyoxyethylene sorbitan esters, lecithin, sodium carboxymethyl cellulose, and methacrylates.

In another embodiment, the method may further include an insect-repellent product selected from a group consisting of nem seed oil, castor oil, dimethyl phtalate, ethyl hexane oil, natural and synthetic oil camphor, pyrthrum, and oil garlic.

In an embodiment where the carrier is ethoxydiglycol, and wherein the complex of essential oils is *Rosmariums Officinalis, Lavaendula Hybrida, Eugenia Caryophyllus, Melaleuca Alternifolia, Cinnamomum Camphora, Mentha Piperita, Cedrus Atlantica, Curcuma Longa, Origanum Compactum*, and *Gaultheria Procumbens*, Musk, the composition further includes a hemp oil, a neem seed extract at 0.25% by weight of azadirachtin, laureth 9, a film-forming agent with thickening, stabilizing and crystallization-inhibiting functions, an antioxidant, and an anti-inflammatory agent.

The composition may further include a delay formula allowing for extended release of the active ingredients. The delay formula may be selected from a group consisting of Beta-cyclodextrins, cyclic natural sugar having a concentration ranging from 2 to 10% by weight of the total composition, cellulose fibers from wood having a concentration ranging from 2 to 10% by weight of the total composition, polymethyl methacrylate and nylon spheres having a concentration ranging from 4 to 12% by weight of the total composition, coated or non-coated silica microreservoirs having a concentration ranging from 2 to 10% by weight of the total composition, linear polyester polymers with a molecular weight of 800 through 5000 Daltons both occlusive and retentive having a concentration ranging from 10 to 20% by weight of the total composition, and a mixture thereof.

The animal is may be a pet. The step of diffusing may include diffusing the composition over an entire skin of the animal. The step of applying may include applying the composition to one or two locations.

The invention is based on the association of a unique and innovating aromatic synergy with other skin hydrating, soothing, antioxidant and nurturing ingredients. Each essential oil that is part of the composition is subject to a precise qualitative definition based on EOBBD (Essential Oil Botanically and Biochemically Defined, ISO 9002 Certified Quality Assurance Process) criteria.

One single application is sufficient for a small size animal. Two will be necessary for a larger size animal.

The presence of the carrier allows for the application of the composition in one or two locations of the skin surface, the diffusion of the product, its storage through the sebaceous glands and its gradual release.

To date, the capacity of the carrier had been used only to provide the animal with an insecticide product. The advantage of the invention is to propose a complete treatment of the skin and coat that has a sanitizing, appeasing and soothing effect on the animal through restoration of a balanced cutaneous ecosystem. The invention makes it possible to prevent inflammatory and infectious disorders of the epiderm and the appeasing and soothing effect of the composition provides the animal with a feeling of well-being and freshness that is a mood stabilizer.

The originality of the composition makes it possible to bathe the animal 48 hours before or after the treatment, while still benefiting from the efficiency of the composition applied for one week minimum.

DETAILED DESCRIPTION OF THE INVENTION

The present invention is a method of treating a coat of an animal, possibly a pet. The method includes the steps of applying a composition to at least one specific location on the coat of the animal. The composition has a carrier being a solvent and at least one complex of essential oils. The composition having active ingredients. The composition is then diffused by an action of the carrier. The active ingredients of the composition are then stored by sebaceous glands of the animal. Finally, the active ingredients are gradually released from the sebaceous glands.

The organic solvent making up the carrier of the method of the present invention is preferably an intermediate polarity solvent, for example: an ethoxydiglycol or butylenes glycol, or propylene glycol, or glycerin in a proportion from 1% to 99% of the total composition in relation to its other components.

More generally, the carrier is chosen from the following group: Acetone, acetonitrile, benzyl alcohol, butyldiglycol, dimethyl acetamide, dimethyl formamide, dipropylene glycol monobutyl ether, ethanol, isopropanol, methanol, ethylene glycol monoethyl ether, monoethyl acetamide, dipropylene glycol monomethyl ether, liquid polyoxyethyleneglycol, propylene glycol, 2-pyrrolidone, including N-methylpyrrolidone, diethyelene glycol monoethyl ether, ethylene glycol, diethyl phtalate, and a mixture of at least two of them.

The above composition can be supplemented by polyunsaturated essential fatty acids to improve the skin surface.

Polyunsaturated fatty acids omega 3 and omega 6 can be introduced by adding hemp seed oil (cannabis sativa) in a proportion that can range from 1% to 15% of the total composition or through natural substitutes such as: fish oil (orange roughy), borage oil (*Borago Officinalis*), coconut oil (*Cocos Nucifera*), kukui oil, sesame oil (*Sesamum indium*), reconstituted synthetic AGPI's or natural extracts, Eicopentaenoic acid (EPA) and docosahexaenoic acid (DHA), shea butter, olive oil (*Olea Europea*), canola oil, walnut oil, soybean oil, and anchusa oil (*Echium Plantagineum*), that can be added to the composition in the proportion of 1 to 99%, more specifically 2% to 50% and preferably 5% to 10% of the total composition.

The composition can also contain a soothing and/or anti-inflammatory and/or anti-pruriginous agent.

Preferably, the soothing agent is laureth 9 in the proportion of 0.8% to 3% or its substitutes, such as: menthol, and its salts, procaine, lidocaine, corticoids, by themselves or in combination of at least two of them.

The laureth 9 polymer is a mixture of polyethylene glycol monolauric ethers with an average of 9 ethylene oxide groups per molecule.

The anti-inflammatory agent can be bisabolol in the proportion of 1% to 5% or its substitutes: natural or synthetic azulene, allantoin, glycyrrhetinic 18 beta acid and its salts in the proportion of 0.01% to 10%, and preferably from 0.01 to 1%, and aloe extracts, *calendula* extracts, carrot extracts, in the proportion of 0.01 to 10%, and preferably from 5 to 10%.

Bisabolol also called alpha-bisabolol has the following formulation:
 1-methyl-4(1,5-dimethyl-1 hydroxyhex-4 (5)-enyl)-cyclohexen-1;
 6-methyl-2-(4-methyl-3-cyclohexen-1-yl)-5-hepten-2 ol.

The above composition contains an antioxidant and anti-radical product: tocopherol or vitamin E, in the form of tocopheryl acetate in the proportion of 0.2% to 2% or its substitutes, such as tocopheryl palmitate or tocopheryl linoleate.

The composition also contains in combination with any one of the above compounds a thickening or stabilizing crystallization-inhibiting film-forming agent, such as polyvinyl pyrrolidone or a product chosen from the following group:

hydroxymethyl cellulose, polyvinyl alcohols, vinyl acetate and vinyl pyrrolidone copolymers, polyethylene glycols, benzyl alcohol, mannitol, glycerol, sorbitol, polyoxyethylene sorbitan esters, lecithin, sodium carboxymethyl cellulose, acrylic derivatives such as methacrylates derived from polyesters of the trimethyl pentanediol/adipic acid type and others.

The composition also contains an insect-repellent product, such as neem seed oil that is in fact *Azadirachta indica* at 0.25% of azadirachtin or its substitutes such as: castor oil (*Ricinus Communis*), diethyl toluamide and butyl acetylaminopropionate, dimethyl phtalate, ethyl hexanediol, natural and synthetic camphor, pyrethrum and derivatives (*Pyrethum Album*), and oil garlic (*Allium Sativum*).

More generally, the composition under the invention can contain the following essential oils by themselves or in combination. *Rosmarinus officinalis* in the proportion of 0.3% to 0.9% with a purifying and soothing sanitizing effect or eucalyptol. *Lavandula hybrida* in the proportion of 0.3% to 0.9% or *lavandula angustifolia* with a deodorant effect. *Eugenia caryophyllus* with an insect-repellent effect, in the proportion of 0.3% to 0.9%. *Melaleuca Alternifolia* or *origan majorana* in the proportion of 0.3% to 0.9% with an anti-infectious effect *Cinnamorum Camphora* or *camphor*, in the proportion of 0.15% to 0.6% with a deodorant and anti-pruriginous effect. *Mentha Piperita* or *mentha orvensis* in the proportion of 0.15% to 0.6% with a deodorant effect. *Cedrus atlantic* ou SAS libanus, in the proportion of 0.15% to 0.6% with an anti-parasitic, cicatrizant and anti-carcinogen effect. *Curcuma longa* or *curcuma zedoaria* in the proportion of 0.15% to 0.6% that also has an anti-parasitic effect. *Origanum compactum* or *origonum vulgare*, in the proportion of 0.06% to 0.3% with an insect-repellent and antimicrobial effect. *Gaultheria procumbens* or its methyl salicylate substitute with a sedative and anti-pruriginous effect. Synthetic musk or musk ketone, in the proportion of 0.06% to 0.3% to perfume or mask natural odors.

The above compounds are used in combination in the composition under the method of the present invention based on the effects sought.

More generally, the essential oils in the attached list can be combined in the composition under the invention.

| ESSENTIAL OIL COMPLEX SUBSTITUTES | | | | |
|---|---|---|---|---|
| *Ajowan* | Almond Tree, Bitter | *Ammi*, Khella | Odorant Dill Seed | *Angelica* |
| White Armose Herb | Basilic | Bay | Bergamot | Rosewood |
| Sandlewood | *Boldo* | Bucchu | Cabreuva | Cajeput |
| *Calamus* | Chamomile, Roman or Noble | Camphor | Cinnamon, Ceylon | Cinnamon, China |
| Cardamones | Carrot | Carvi | Catmin | Cedarwood, Atlas |
| Cedarwood, Virginia | Celeri | *Chenopodium Vermifuge.* | Rockrose, Labdanum-Bearing | Yellow Lemon |
| *Citronnella*, Ceylon | *Citronnella*, Java | Copahu | Coriander | Cubeb |
| Cumin | *Curcuma* | Evergreen Cypress | Douglas | Elemi |
| Incense | Black Spruce | Tarragon | *Eucalyptus* | Lignum Vitae |
| Galbanum | *Gaultheria*, Wintergreen | Juniper | *Geranium*, Odorant | Ginger |
| Clove Tree | *Helichrysum* | Hyssop with lying down branches | *Hyssopus Officinalis* | *Inula* |
| Iormenie, Wild Chamomile | *Lantana* | *Laurus Nobilis* | Spike Lavender |
| *Lavandula Officinalis* | *Stoechas* Lavender | *Lavandula Hybrida* | Lemongrass |
| *Pistacia Lentiscus* | *Lepstospermum* | Sweet Lime | *Litsea* |
| Lovage | Red Mandarin | Sweet Marjoram | *Majorana Sylvestris* |
| Wild Marjoram | *Matricaria* | Larch | *Melissa Officinalis* |
| Wild Mint | Peppermint | Pennyroyal | Yarrow |
| St. Johns-wort | Nutmeg | Myrrh | Myrtle |
| Spikenard | Niaouli | Orange Tree | Sweet Orange |
| *Origanum* | Spanish *Origanum* | *Origanum Vulgare* | Palmarosa |
| Grapefruit | Patchouli | Parsley | Landes Pine |
| *Pinus Syvestris* | Black Pepper | Aromatic Vinyl Pyrrolidone | *Rosemarinus Officinalis* |
| Pyramidal Rosemary | Bulgarian Rose | Sandalwood *Amyris* | *Santolina* Dwarf Cypress |
| Balsam Fir | Siberian Fir | Silver Fir | Savory |
| *Sassafras* | Small Leaf Sage | *Salvia Officinalis* | Clary |
| Wild Thyme | Blue Tansy | Tea tree | Turpentine |
| Thuya | Thyme | Savory Leaf Thyme | Goldenrod |
| Fleabane | Lemon Verbena | Vetiver | Ylang-ylang, Full Distillation |
| Ylang-ylang, First Batch | | | |

The essential oils were selected based on precise specifications with regard to the active ingredients they contain. Among the active ingredients can be found in particular sesquiterpenes with anti-inflammatory properties, phenol compounds with locally immunostimulating and anti-infectious properties, other phenol compounds (eugenol et carvacrol) with insectifuge and repellent effects and esters with antalgesic and decongestant properties they may temper, even prevent, a possibly irritant action of the phenols on the skin.

A formula especially suited for the composition under the invention contains: As carrier and skin solvent, an ethoxydiglycol. As vegetal oil rich in polyunsaturated fatty acids, hemp oil (cannabis sativa). As concentrated essential oils: *Rosmarius Officinalis, Lavendula Hybrida, Eugenia Caryophyllus, Melaleuca Alternifolia, Cinnamomum Camphora, Mentha Piperita, Cedrus Atlantica, Curcuma Longa, Origanum Compactum, Gaultheria Procumbens*, Musk. As insect repellent and soothing product, neem seed extract (*azadirachta Indica*) at 0.25% of azadirachtin). As soothing, desensitizing and anti-pruriginous ingredients, laureth 9. As thickening, stabilizing crystallization-inhibiting agent forming a film on the animal skin, polyvinyl pyrrolidone as mentioned above in the description. A vitamin E with antioxidant function, such as D alpha tocopherol or tocopheryl acetate, or the products mentioned above in the description, or the products mentioned above (other antioxidants): butyl hydroxyanisole, butyl hydroxytoluene, ascorbic acid, sodium metabisulfate, propyl gallate, sodium thiosulfate, mixture of no more than two of them. An anti-inflammatory agent such as alpha-bisabolol, bisabolol or its substitutes as mentioned above in the description.

The formulation active ingredients can be included in whole or in part in a "delay" formulation allowing for extended release time and thus extended action duration of these active ingredients. The compounds allowing for that modification can be chosen among beta-cyclodextrins, silica, cellulose fibers, nylon, poly-methacrylates.

A delay or scheduled release formula can allow for extended release of the active ingredients up to twenty-eight days after application. The delay formulas use: beta-cyclodextrins, cyclic natural sugars: present in the formulation with a concentration ranging from 2 to 10%; and/or cellulose fibers from wood: present in the formulation with a concentration ranging from 2 to 10%; and/or polymethyl methacrylate and nylon spheres: present in the formulation with a concentration ranging from 4 to 12%; and/or coated or non-coated silica microreservoirs: present in the formulation with a concentration ranging from 2 to 10%; and/or linear polyester polymers with a molecular weight of 800 through 5000 Daltons both occlusive and retentive: present in the formulation with a concentration ranging from 10 to 20%.

The proportions of each component are taken in the above-mentioned percentage values, said values being expressed in percentages of the total and full composition.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A method of treating a coat of a pet, the method comprising:
   preparing a composition, the composition having at least one complex of essential oils, polyunsaturated fatty acids and active ingredients, the polyunsaturated fatty acids being omega 3 and omega 6 that are introduced by adding hemp seed oil in a proportion of between 1% and 15% by weight of the composition or by adding natural substitutes for hemp seed oil in an amount of between 5% and 10% of the composition, said composition having a carrier suitable for diffusing the composition on the coat;
   locally applying said composition to only a part of the coat;
   diffusing the applied composition solely by action of said carrier from the part of the coat over the entire coat of the pet; and
   maintaining the diffused composition on the coat for several days such that sebaceous glands of the pet store and gradually release the active ingredients of the diffused composition.

2. The method of claim 1, wherein the carrier includes ethoxydiglycol.

3. The method of claim 1, wherein said carrier includes an organic solvent selected from the group consisting of acetone, acetonitrile, benzyl alcohol, butyldiglycol, dimethyl acetamide, dimethyl formamide, dipropylene glycol monobutyl ether, ethanol, isopropanol, methanol, ethylene glycol monoethyl ether, monoethyl acetamide, dipropylene glycol monomethyl ether, liquid polyoxyethylene-glycol, propylene glycol, 2-pyrrolidone including N-methyl pyrrolidone, diethylene glycol monoethyl ether, ethylene glycol, diethyl phtalate, and mixtures thereof.

4. The method of claim 1, wherein the fatty acids are selected from the group consisting of fish oil, borage oil, coconut oil, kukui oil, sesame oil, reconstituted synthetic polyunsaturated fatty acids, eicosapentaenoic acid, docosahexaenoic acid, shea butter, canola oil, walnut oil, soybean oil, and anchusa oil in a proportion of 3 to 50% by weight of the total composition.

5. A method of treating a coat of a pet, the method comprising:
   preparing a composition, the composition having at least one complex of essential oils, polyunsaturated fatty acids and active ingredients and a soothing agent, the polyunsaturated fatty acids being omega 3 and omega 6 that are introduced by adding hemp seed oil in a proportion of between 1% and 15% by weight of the composition or by adding natural substitutes for hemp seed oil in an amount of between 5% and 10% of the composition, said composition having a carrier suitable for diffusing the composition on the coat;
   locally applying said composition to only a part of the coat;
   diffusing the applied composition solely by action of said carrier from the part of the coat over the entire coat of the pet; and
   maintaining the diffused composition on the coat for several days such that sebaceous glands of the pet store and gradually release the active ingredients of the diffused composition.

6. A method of treating a coat of a pet, the method comprising:
   preparing a composition, the composition having at least one complex of essential oils, polyunsaturated fatty acids and active ingredients and an anti-inflammatory agent, the polyunsaturated fatty acids being omega 3 and omega 6 that are introduced by adding hemp seed oil in a proportion of between 1% and 15% by weight of the composition or by adding natural substitutes for hemp seed oil in an amount of between 5% and 10% of the composition, said composition having a carrier suitable for diffusing the composition on the coat;
   locally applying said composition to only a part of the coat;
   diffusing the applied composition solely by action of said carrier from the part of the coat over the entire coat of the pet; and
   maintaining the diffused composition on the coat for several days such that sebaceous glands of the pet store and gradually release the active ingredients of the diffused composition.

7. The method of claim 6, wherein the anti-inflammatory agent is selected from the group consisting of bisabolol, azulene, allantoin, 18-beta glycyrrhetinic acid and its salts, aloe extracts, calendula extracts, and carrot extracts in a proportion of 0.01 to 10% by weight of the total composition.

8. A method of treating a coat of a pet, the method comprising:
   preparing a composition, the composition having at least one complex of essential oils, polyunsaturated fatty acids and active ingredients an anti-pruriginous agent, the polyunsaturated fatty acids being omega 3 and omega 6 that are introduced by adding hemp seed oil in a proportion of between 1% and 15% by weight of the composition or by adding natural substitutes for hemp seed oil in an amount of between 5% and 10% of the composition, said composition having a carrier suitable for diffusing the composition on the coat;
   locally applying said composition to only a part of the coat;
   diffusing the applied composition solely by action of said carrier from the part of the coat over the entire coat of the pet; and
   maintaining the diffused composition on the coat for several days such that sebaceous glands of the pet store and gradually release the active ingredients of the diffused composition.

9. The method of claim 1, the composition further comprising:
   a thickening or stabilizing crystallization-inhibiting film-forming agent selected from the group consisting of polyvinyl pyrrolidone, hydroxymethyl cellulose, polyvinyl alcohols, vinyl acetate and vinyl pyrrolidone copolymers, polyethylene glycols, benzyl alcohol, mannitol, glycerol, sorbitol, polyoxyethylene sorbitan esters, lecithin, sodium carboxymethyl cellulose, and methacrylates.

10. The method of claim 1, the composition further comprising:
   an insect-repellent product selected from the group consisting of neem seed oil, castor oil, dimethyl phthalate, ethyl hexane oil, natural and synthetic oil camphor, pyrethrum, and garlic oil.

11. The method of claim 1, wherein the carrier is ethoxydiglycol, wherein the essential oils are *Rosmarinus officinalis, Lavandula hybrida, Eugenia caryophyllus, Melaleuca alternifolia, Cinnamomum camphora, Mentha piperita, Cedrus atlantica, Curcuma longa, Origanum compactum*, and *Gaultheria procumbens*, and musk, said composition further comprising:
   a hemp oil, a neem seed extract at 0.25% by weight of azadirachtin, laureth 9, a film-forming agent with thickening, stabilizing and crystallization-inhibiting functions, an antioxidant, and an anti-inflammatory agent.

12. The method of claim 1, the composition further comprising:
   a delay formula allowing for extended release of said active ingredients.

13. The method of claim 12, wherein said delay formula is selected from the group consisting of Beta-cyclodextrins, cyclic natural sugar having a concentration ranging from 2 to 10% by weight of the total composition, cellulose fibers from wood having a concentration ranging from 2 to 10% by weight of the total composition, polymethyl methacrylate and nylon spheres having a concentration ranging from 4 to 12% by weight of the total composition, coated or non-coated silica microreservoirs having a concentration ranging from 2 to 10% by weight of the total composition, linear polyester polymers with a molecular weight of 800 through 5000 Daltons both occlusive and retentive having a concentration ranging from 10 to 20% by weight of the total composition, and a mixture thereof.

* * * * *